United States Patent

Maurer et al.

[11] 4,188,383
[45] Feb. 12, 1980

[54] COMBATING ARTHROPODS WITH O-ALKYL-O-(6-DIALKYL-CARBAMOYLOXY-PYRIMIDIN-4-YL)-(THIONO)(THIOL)-PHOSPHORIC (PHOSPHONIC) ACID ESTERS AND ESTER-AMIDES

[75] Inventors: Fritz Maurer, Wuppertal; Ingeborg Hammann, Cologne, both of Fed. Rep. of Germany

[73] Assignee: Bayer Aktiengesellschaft, Leverkusen, Fed. Rep. of Germany

[21] Appl. No.: 879,423

[22] Filed: Feb. 21, 1978

[30] Foreign Application Priority Data

Mar. 8, 1977 [DE] Fed. Rep. of Germany ....... 2709908

[51] Int. Cl.$^2$ .............................. A01N 9/36; C07F 9/65
[52] U.S. Cl. ..................................... 424/200; 544/243
[58] Field of Search ....................... 544/243; 424/200

[56] References Cited

U.S. PATENT DOCUMENTS

| | | | |
|---|---|---|---|
| 2,754,243 | 7/1956 | Gysin | 167/33 |
| 3,639,616 | 2/1972 | Lichtman | 424/300 |
| 3,862,188 | 1/1975 | Milzner | 260/251 P |
| 4,045,561 | 8/1977 | Muhle | 424/251 |

OTHER PUBLICATIONS

Metcalf, R. L. et al., J. Economic Entomology, vol. 55, No. 6, pp. 889–894.

*Primary Examiner*—Alton D. Rollins
*Assistant Examiner*—Lisa Jones
*Attorney, Agent, or Firm*—Sprung, Felfe, Horn, Lynch & Kramer

[57] ABSTRACT

O-Alkyl-O-(6-dialkylcarbamoyloxy-pyrimidin-4-yl)-(thiono)(thiol)-phosphoric (phosphonic) acid esters and esteramides of the formula

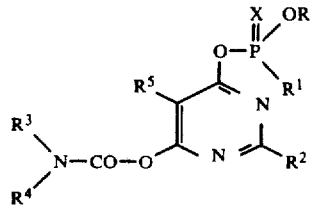

in which
R is alkyl,
$R^1$ is alkoxy, alkylthio, alkylamino, alkyl or phenyl,
$R^2$ is hydrogen, alkyl, alkoxy, alkylthio, alkylamino or phenyl,
$R^3$ and $R^4$ each independently is alkyl,
$R^5$ is hydrogen, alkyl or halogen, and
X is oxygen or sulphur,
which possess arthropodicidal properties.

10 Claims, No Drawings

COMBATING ARTHROPODS WITH O-ALKYL-O-(6-DIALKYL-CARBAMOYLOXY-PYRIMIDIN-4-YL)-(THIONO)(THIOL)-PHOSPHORIC (PHOSPHONIC) ACID ESTERS AND ESTER-AMIDES

The present invention relates to and has for its objects the provision of particular new O-alkyl-O-(6-dialkylcarbamoyloxypyrimidin-4-yl)-(thiono)(thiol)-phosphoric (phosphonic) acid esters and ester-amides which possess arthropodicidal properties, active compositions in the form of mixtures of such compounds with solid and liquid dispersible carrier vehicles, and methods for producing such compounds and for using such compounds in a new way especially for combating pests, e.g. arthropods, with other and further objects becoming apparent from a study of the within specification and accompanying examples.

It has already been disclosed that certain pyrimidinyl-mono- and di-thiophosphoric acid esters, for example O,O-dimethyl-O-[2-ethyl-4-ethoxy-pyrimidin-6-yl]- and O,O-diethyl-O-[2-isopropyl-4-methyl-pyrimidin-6-yl]-thionophosphoric acid ester and O-ethyl-S-n-propyl-O-[2-isopropyl-4-methyl-pyrimidin-6-yl]-thionothiolphosphoric acid ester, possess insecticidal and acaricidal properties (see U.S. Pat. Nos. 2,754,243 and 3,862,188 and 3,951,975).

The present invention now provides, as new compounds, the carbamoyloxy-substituted pyrimidinyl(thiono)(thiol)phosphoric(phosphonic) acid esters and ester-amides of the general formula

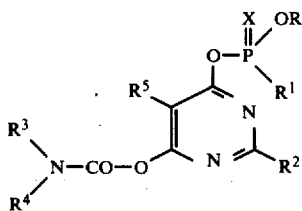

(I)

in which
R represents alkyl,
$R^1$ represents alkoxy, alkylthio, alkylamino, alkyl or phenyl,
$R^2$ represents hydrogen, alkyl, alkoxy, alkylthio, alkylamino or phenyl,
$R^3$ and $R^4$, which may be identical or different, each represent alkyl,
$R^5$ represents hydrogen, alkyl or halogen and
X represents oxygen or sulphur.

Preferably, R represents straight-chain or branched alkyl with 1 to 6 (especially 1 to 4) carbon atoms, $R^1$ represents straight-chain or branched alkyl or alkoxy each with 1 to 5 (especially 1 to 3) carbon atoms, straight-chain or branched alkylthio or monoalkylamino each with 1 to 6 (especially 1 to 4) carbon atoms, or phenyl, $R^2$ represents hydrogen, phenyl, straight-chain or branched alkyl or alkoxy each with 1 to 6 (especially 1 to 4) carbon atoms, or straight-chain or branched alkylthio or dialkylamino each with 1 to 5 (especially 1 to 3) carbon atoms per alkyl moiety, $R^3$ and $R^4$ are identical and each represent straight-chain or branched alkyl with 1 to 4 (preferably 1 or 2) carbon atoms, $R^5$ represents hydrogen, methyl, chlorine or bromine and X represents sulphur.

Surprisingly, the carbamoyloxy-substituted pyrimidinyl-(thiono)(thiol)-phosphoric(phosphonic) acid esters and ester-amides according to the invention exhibit a substantially better insecticidal and acaricidal action than the corresponding pyrimidinyl-mono- and di-thiophosphoric acid esters of analogous structure and of the same type of action. The products of the present invention thus represent a genuine enrichment of the art.

The invention also provides a process for the preparation of a carbamoyloxy-substituted pyrimidinyl(thiono)(thiol)-phosphoric(phosphonic) acid ester or ester-amide of the formula (I) in which (a) a 6-hydroxy-pyrimidinyl(thiono)(thiol)-phosphoric(phosphonic) acid ester or ester-amide of the general formula

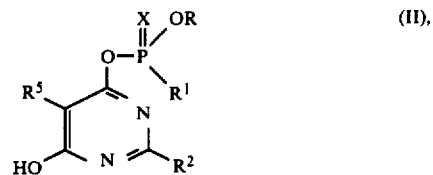

(II), in which
R, $R^1$, $R^2$, $R^5$ and X have the above-mentioned meanings, is reacted with an N,N-dialkylcarbamic acid halide of the general formula

(III), in which
$R^3$ and $R^4$ have the above-mentioned meanings and Hal represents halogen, preferably chlorine, if appropriate in the presence of an acid acceptor and, if appropriate, in the presence of a solvent or diluent, or (b) a(thiono)(thiol)-phosphoric(phosphonic) acid ester halide or ester-amide halide of the general formula

(IV), in which
R, $R^1$ and X have the above-mentioned meanings and $Hal^1$ represents halogen, preferably chlorine, is reacted with an N,N-dialkylcarbamic acid ester of the general formula

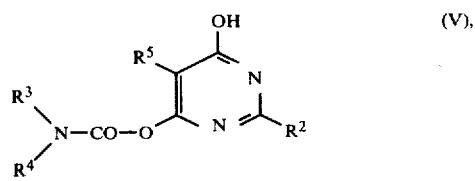

(V), in which
$R^2$, $R^3$, $R^4$ and $R^5$ have the above-mentioned meanings, if appropriate, in the presence of an acid acceptor and, if appropriate, in the presence of a solvent or diluent.

If, for example, following process variant (a), O,O-diethyl-O-[5-methyl-6-hydroxy-pyrimidin-4-yl]-thionophosphoric acid ester and N,N-diethylcarbamic acid chloride, and, following process variant (b), O-ethyl-thionophenylphosphonic acid ester chloride and N,N-diethyl-O-[2-isopropyl-4-hydroxy-pyrimidin-6-yl]-carbamic acid ester are used as starting materials, the courses of the reactions can be represented by the following equations:

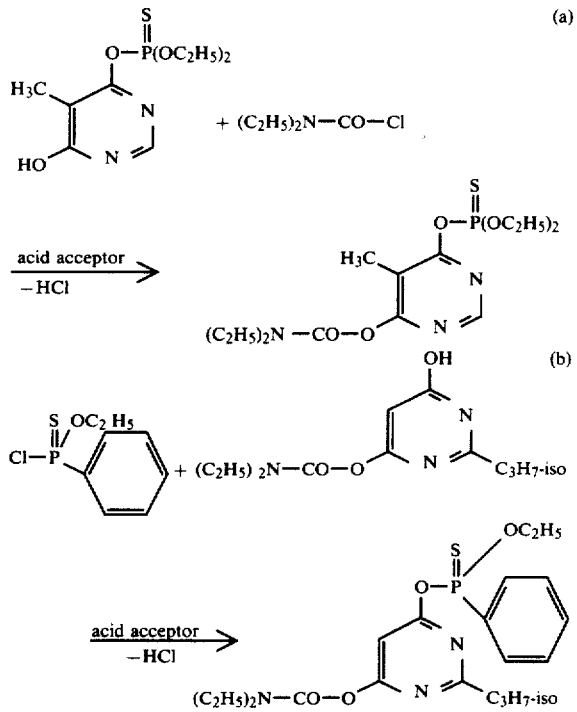

The 6-hydroxy-pyrimidinyl(thiono)(thiol)-phosphoric (phosphonic) acid esters and ester-amides (II) to be used as starting materials can be prepared in accordance with generally customary processes described in the literature, for example by reacting 4,6-dihydroxy-pyrimidines with (thiono)(thiol)-phosphoric(phosphonic) acid ester halides or ester-amide halides, if appropriate in the presence of an acid acceptor and, if appropriate, in the presence of a solvent, in accordance with the following equation:

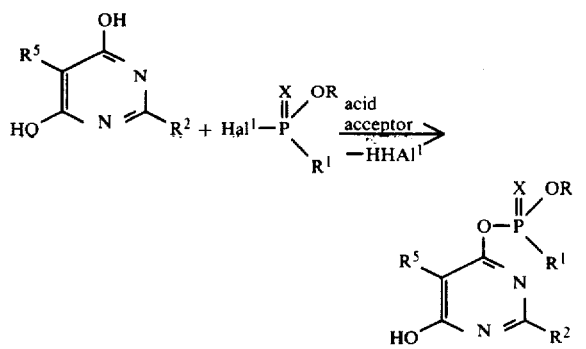

wherein
R, $R^1$, $R^2$, $R^5$, X and $Hal^1$ have the above-mentioned meanings.

The following may be mentioned as individual examples of these starting compounds: O-[6-hydroxy-pyrimidin-4-yl]-, O-[2-methyl-6-hydroxy-pyrimidin-4-yl]-, O-[2-ethyl-6-hydroxy-pyrimidin-4-yl]-, O-[2-n-propyl-6-hydroxy-pyrimidin-4-yl]-, O-[2-iso-propyl-6-hydroxy-pyrimidin-4-yl]-, O-[2-n-butyl-6-hydroxy-pyrimidin-4-yl]-, O-[2-iso-butyl-6-hydroxy-pyrimidin-4-yl]-, O-[2-sec.-butyl-6-hydroxy-pyrimidin-4-yl]-, O-[2-tert.-butyl-6-hydroxy-pyrimidin-4-yl]-, O-[2-methoxy-6-hydroxy-pyrimidin-4-yl]-, O-[2-ethoxy-6-hydroxy-pyrimidin-4-yl]-, O-[2-n-propoxy-6-hydroxy-pyrimidin-4-yl]-, O-[2-iso-propoxy-6-hydroxy-pyrimidin-4-yl]-, O-[2-n-butoxy-6-hydroxy-pyrimidin-4-yl]-, O-[2-isobutoxy-6-hydroxy-pyrimidin-4-yl]-, O-[2-sec.-butoxy-6-hydroxy-pyrimidin-4-yl]-, O-[2-tert.-butoxy-6-hydroxy-pyrimidin-4-yl]-, O-[2-methylthio-6-hydroxy-pyrimidin-4-yl]-, O-[2-ethylthio-6-hydroxy-pyrimidin-4-yl]-, O-[2-n-propylthio-6-hydroxy-pyrimidin-4-yl]-, O-[2-iso-propylthio-6-hydroxy-pyrimidin-4-yl]-, O-[2-dimethylamino-6-hydroxy-pyrimidin-4-yl]-, O-[2-diethylamino-6-hydroxy-pyrimidin-4-yl]-, O-[2-di-n-propyl-amino-6-hydroxy-pyrimidin-4-yl]-, O-[2-phenyl-6-hydroxy-pyrimidin-4-yl]-, O-[5-methyl-6-hydroxy-pyrimidin-4-yl]-, O-[5-chloro-6-hydroxy-pyrimidin-4-yl]-, O-[5-bromo-6-hydroxy-pyrimidin-4-yl]-, O-[2-methyl-5-chloro-6-hydroxy-pyrimidin-4-yl]-, O-[2-ethyl-5-chloro-6-hydroxy-pyrimidin-4-yl]-, O-[2-n-propyl-5-chloro-6-hydroxy-pyrimidin-4-yl]-, O-[2-iso-propyl-5-chloro-6-hydroxy-pyrimidin-4-yl]-, O-[2-n-butyl-5-chloro-6-hydroxy-pyrimidin-4-yl]-, O-[2-iso-butyl-5-chloro-6-hydroxy-pyrimidin-4-yl]-, O-[2-sec.-butyl-5-chloro-6-hydroxy-pyrimidin-4-yl]-, O-[2-tert.-butyl-5-chloro-6-hydroxy-pyrimidin-4-yl]-, O-[2-methoxy-5-chloro-6-hydroxy-pyrimidin-4-yl]-, O-[2-ethoxy-5-chloro-6-hydroxy-pyrimidin-4-yl]-, O-[2-n-propoxy-5-chloro-6-hydroxy-pyrimidin-4-yl]-, O-[2-iso-propoxy-5-chloro-6-hydroxy-pyrimidin-4-yl]-, O-[2-n-butoxy-5-chloro-6-hydroxy-pyrimidin-4-yl]-, O-[2-iso-butoxy-5-chloro-6-hydroxy-pyrimidin-4-yl]-, O-[2-sec.-butoxy-5-chloro-6-hydroxy-pyrimidin-4-yl]-, O-[2-tert.-butoxy-5-chloro-6-hydroxy-pyrimidin-4-yl]-, O-[2-methylthio-5-chloro-6-hydroxy-pyrimidin-4-yl]-, O-[2-ethylthio-5-chloro-6-hydroxy-pyrimidin-4-yl]-, O-[2-n-propylthio-5-chloro-6-hydroxy-pyrimidin-4-yl]-, O-[2-iso-propylthio-5-chloro-6-hydroxy-pyrimidin-4-yl]-, O-[2-dimethylamino-5-chloro-6-hydroxy-pyrimidin-4-yl]-, O-[2-diethylamino-5-chloro-6-hydroxy-pyrimidin-4-yl]-, O-[2-di-n-propylamino-5-chloro-6-hydroxy-pyrimidin-4-yl]-, O-[2-phenyl-5-chloro-6-hydroxy-pyrimidin-4-yl]-, O-[2-methyl-5-bromo-6-hydroxy-pyrimidin-4-yl]-, O-[2-ethyl-5-bromo-6-hydroxy-pyrimidin-4-yl]-, O-[2-n-propyl-5-bromo-6-hydroxy-pyrimidin-4-yl]-, O-[2-iso-propyl-5-bromo-6-hydroxy-pyrimidin-4-yl]-, O-[2-n-butyl-5-bromo-6-hydroxy-pyrimidin-4-yl]-, O-[2-iso-butyl-5-bromo-6-hydroxy-pyrimidin-4-yl]-, O-[2-sec.-butyl-5-bromo-6-hydroxy-pyrimidin-4-yl]-, O-[2-tert.-butyl-5-bromo-6-hydroxy-pyrimidin-4-yl]-, O-[2-methoxy-5-bromo-6-hydroxy-pyrimidin-4-yl]-, O-[2-ethoxy-5-bromo-6-hydroxy-pyrimidin-4-yl]-, O-[2-n-propoxy-5-bromo-6-hydroxy-pyrimidin-4-yl]-, O-[2-iso-propoxy-5-bromo-6-hydroxy-pyrimidin-4-yl]-, O-[2-n-butoxy-5-bromo-6-hydroxy-pyrimidin-4-yl]-, O-[2-iso-butoxy-5-bromo-6-hydroxy-pyrimidin-4-yl]-, O-[2-sec.-butoxy-5-bromo-6-hydroxy-pyrimidin-4-yl]-, O-[2-tert.-butoxy-5-bromo-6-hydroxy-pyrimidin-4-yl]-, O-[2-methylthio-5-bromo-6-hydroxy-pyrimidin-4-yl]-, O-[2-ethyl-thio-5-bromo-6-hydroxy-pyrimidin-4-yl]-, O-[2-n-propylthio-5-bromo-6-hydroxy-pyrimidin-4-yl]-, O-[2-iso-propylthio-5-bromo-6-hydroxy-pyrimidin-4-yl]-, O-[2-dimethylamino-5-bromo-6-hydroxy-pyrimidin-4-yl]-, O-[2-diethylamino-5-bromo-6-hydroxy-pyrimidin- 4-yl]-, O-[2-di-n-propylamino-5-bromo-6-hydroxy-pyrimidin-4-yl]-, O-[2-phenyl-5-bromo-6-hydroxy-pyrimidin-4-yl]-, O-[2,5-dimethyl-6-hydroxy-pyrimidin-4-yl]-, O-[2-ethyl-5-methyl-6-hydroxy-pyrimidin-4-yl]-, O-[2-n-propyl-5-methyl-6-hydroxy-pyrimidin-4-yl]-, O-[2-iso-propyl-5-methyl-6-hydroxy-pyrimidin-4-yl]-, O-[2-n-butyl-5-methyl-6-hydroxy-pyrimidin-4-yl]-, O-[2-iso-butyl-5-methyl-6-hydroxy-pyrimidin-4-yl]-, O-[2-sec.-butyl-5-methyl-6-hydroxy-pyrimidin-4-yl]-, O-[2-tert.-butyl-5-methyl-6-hydroxy-pyrimidin-4-yl]-, O-[2-methoxy-5-methyl-6-hydroxy-pyrimidin-4-yl]-, O-[2-ethoxy-5-methyl-6-hydroxy-pyrimidin-4-yl]-, O-[2-n-propoxy-5-methyl-6-hydroxy-pyrimidin-4-yl]-, O-[2-iso-propoxy-5-methyl-6-hydroxy-pyrimidin-4-yl]-, O-[2-n-butoxy-5-methyl-6-hydroxy-pyrimidin-4-yl]-, O-[2-iso-butoxy-5-methyl-6-hydroxy-pyrimidin-4-yl]-, O-[2-sec.-butoxy-5-methyl-6-hydroxy-pyrimidin-4-yl]-, O-[2-tert.-butoxy-5-methyl-6-hydroxy-pyrimidin-4-yl]-, O-[2-methylthio-5-methyl-6-hydroxy-pyrimidin-4-yl]-, O-[2-ethylthio-5-methyl-6-hydroxy-pyrimidin-4-yl]-, O-[2-n-propylthio-5-methyl-6-hydroxy-pyrimidin-4-yl]-, O-[2-iso-propyl-thio-5-methyl-6-hydroxy-pyrimidin-4-yl]-, O-[2-dimethylamino-5-methyl-6-hydroxy-pyrimidin-4-yl]-, O-[2-diethylamino-5-methyl-6-hydroxy-pyrimidin-4-yl]-, O-[2-di-n-propylamino-5-methyl-6-hydroxy-pyrimidin-4-yl]-, and O-[2-phenyl-5-methyl-6-hydroxy-pyrimidin-4-yl]-O,O-dimethyl-, -O,O-diethyl-, -O,O-di-n-propyl-, -O,O-di-iso-propyl-, -O,O-di-n-butyl-, -O,O-di-iso-buty-, -O,O-di-sec.-butyl-, O-methyl-O-ethyl-, -O-methyl-O-n-propyl-, -O-methyl-O-iso-propyl-, -O-methyl-O-n-butyl-, -O-methyl-O-iso-butyl-, -O-methyl-O-sec.-butyl-, -O-methyl-O-tert.-butyl-, -O-ethyl-O-n-propyl-, -O-ethyl-O-iso-propyl-, -O-ethyl-O-n-butyl-, -O-ethyl-O-sec.-butyl-, -O-ethyl-O-iso-butyl-, -O-n-propyl-O-butyl-, or -O-iso-propyl-O-butyl-phosphoric acid ester and the corresponding thiono analogues; -O,S-dimethyl-, -O,S-diethyl-, -O,S-di-n-propyl-, -O,S-di-iso-propyl-, -O,S-di-n-butyl-, -O,S-di-iso-butyl-, -O,S-di-tert.-butyl-, -O-ethyl-S-n-propyl-, -O-ethyl-S-iso-propyl-, -O-ethyl-S-n-butyl-, -O-ethyl-S-sec.-butyl-, -O-n-propyl-S-ethyl-, -O-n-propyl-S-iso-propyl-, -O-n-butyl-S-n-propyl- and -O-sec.-butyl-S-ethyl-thiolphosphoric acid ester and the corresponding thiono analogues; -O-methyl-, -O-ethyl-, -O-n-propyl-, -O-iso-propyl-, -O-n-butyl-, -O-iso-butyl-, -O-sec.-butyl-, -O-tert.-butyl- methane-, -ethane-, -n-propane-, -iso-propane-, -n-butane-, -iso-butane-, -tert.-butane-, -sec-butane- and -phenyl-phosphonic acid ester and the corresponding thiono analogues; and -O-methyl-N-methyl-, -O-methyl-N-ethyl-, -O-methyl-N-n-propyl-, -O-methyl-N-iso-propyl-, -O-ethyl-N-methyl-, -O-ethyl-N-ethyl-, O-ethyl-N-n-propyl-, -O-ethyl-N-iso-propyl-, -O-n-propyl-N-methyl-, -O-n-propyl-N-ethyl-, O-n-propyl-N-n-propyl-, O-n-propyl-N-isopropyl-, -O-iso-propyl-N-methyl-, -O-iso-propyl-N-ethyl-, -O-iso-propyl-N-n-propyl-, -O-iso-propyl-N-iso-propyl-, -O-n-butyl-N-methyl-, -O-n-butyl-N-ethyl-, -O-n-butyl-N-n-propyl-, -O-n-butyl-N-iso-propyl-, -O-tert.-butyl-N-methyl-, -O-tert.-butyl-N-ethyl-, -O-tert.-butyl-N-n-propyl-, -O-tert.-butyl-N-iso-propyl-, -O-iso-butyl-N-methyl-, -O-iso-butyl-N-ethyl-, -O-sec.-butyl-N-methyl- and -O-sec.-butyl-N-ethyl-phosphoric acid ester amide and the corresponding thiono analogues.

The N,N-dialkylcarbamic acid halides (III) also to be used as starting materials are known and can readily be prepared, even on an industrial scale, in accordance with processes known from the literature. The following may be mentioned as individual examples thereof: N,N-dimethyl- and N,N-diethyl-carbamic acid chloride.

Further starting materials are the (thiono)(thiol)-phosphoric(phosphonic) acid ester halides and ester-amide halides (IV), which are known from the literature. The following may be mentioned as individual examples thereof: O,O-dimethyl-, O,O-diethyl-, O,O-di-n-propyl-, O,O-di-iso-propyl-, O-methyl-O-ethyl-, O-methyl-O-n-propyl-, O-methyl-O-iso-propyl-, O-methyl-O-n-butyl-, O-methyl-O-iso-butyl-, O-methyl-O-sec.-butyl-, O-methyl-O-tert.-butyl-, O-ethyl-O-n-propyl-, O-ethyl-O-isopropyl-, O-ethyl-O-n-butyl-, O-ethyl-O-sec.-butyl-, O-ethyl-O-iso-butyl-, O-n-propyl-O-butyl- and O-iso-propyl-O-butyl-phosphoric acid diester chloride and the corresponding thiono analogues; O-methyl-, O-ethyl-, O-n-propyl-, O-iso-propyl-, O-n-butyl-, O-iso-butyl-, O-sec.-butyl- and O-tert.-butyl-methane-, -ethane-, -n-propane-, -iso-propane-, -n-butane-, -iso-butane-, -tert.-butane-, -sec.-butane- and -phenyl-phosphonic acid ester chloride and the corresponding thiono analogues; O,S-dimethyl-, O,S-diethyl-, O,S-di-n-propyl-, O,S-di-iso-prcpyl-, O,S-di-n-butyl-, O,S-di-iso-butyl-, O-ethyl-S-n-propyl-, O-ethyl-S-iso-propyl-, O-ethyl-S-n-butyl-, O-ethyl-S-sec.-butyl-, O-n-propyl-S-ethyl-, O-n-propyl-S-iso-propyl-, O-n-butyl-S-n-propyl- and O-sec.-butyl-S-ethyl-thiolphosphoric acid diester chloride and the corresponding thiono analogues; and O-methyl-N-methyl-, O-methyl-N-ethyl-, O-methyl-N-n-propyl-, O-methyl-N-iso-propyl-, O-ethyl-N-methyl-, O-ethyl-N-ethyl-, O-ethyl-N-n-propyl-, O-ethyl-N-iso-propyl-, O-n-propyl-N-methyl-, O-n-propyl-N-ethyl-, O-n-propyl-N-n-propyl-, O-n-propyl-N-iso-propyl-, O-iso-propyl-N-methyl-, O-iso-propyl-N-ethyl-, O-iso-propyl-N-n-propyl-, O-iso-propyl-N-iso-propyl-, O-n-butyl-N-methyl-, O-n-butyl-N-ethyl-, O-n-butyl-N-n-propyl-, O-n-butyl-N-iso-propyl-, O-iso-butyl-N-methyl-, O-iso-butyl-N-ethyl-, O-iso-butyl-N-n-propyl-, O-iso-butyl-N-iso-propyl-, O-sec.-butyl-N-methyl-, O-sec.-butyl-N-ethyl-, O-sec.-butyl-N-n-propyl- and O-sec.-butyl-N-iso-propyl-phosphoric acid monoester-amide chloride and the corresponding thiono analogues.

The N,N-dialkylcarbamic acid esters (V) are also used as starting materials; these are obtained from the known 4,6-dihydroxypyrimidine derivatives by reaction with N,N-dialkyl-carbamic acid halides or with phosgene and then with dialkylamines. The following may be mentioned as individual examples: O-[4-hydroxy-pyrimidin-6-yl]-, O-[2-methyl-4-hydroxy-pyrimidin-6-yl]-, O-[2-ethyl-4-hydroxy-pyrimidin-6-yl]-, O-[2-n-propyl-4-hydroxy-pyrimidin-6-yl]-, O-[2-iso-propyl-4-hydroxy-pyrimidin-6-yl]-, O-[2-n-butyl-4-hydroxy-pyrimidin-6-yl]-, O-[2-iso-butyl-4-hydroxy-pyrimidin-6-yl]-, O-[2-sec.-butyl-4-hydroxy-pyrimidin-6-yl]-, O-[2-tert.-butyl-4-hydroxy-pyrimidin-6-yl]-, O-[2-methoxy-4-hydroxy-pyrimidin-6-yl]-, O-[2-ethoxy-4-hydroxy-pyrimidin-6-yl]-, O-[2-n-propoxy-4-hydroxy-pyrimidin-6-yl]-, O-[2-iso-propoxy-4-hydroxy-pyrimidin-6-yl]-, O-[2-n-butoxy-4-hydroxy-pyrimidin-6-yl]-, O-[2-iso-butoxy-4-hydroxy-pyrimidin-6-yl]-, O-[2-sec.-butoxy-4-hydroxy-pyrimidin-6-yl]-, O-[2-tert.-butoxy-4-hydroxy-pyrimidin-6-yl]-, O-[2-methylthio-4-hydroxy-pyrimidin-6-yl]-, O-[2-ethylthio-4-hydroxy-pyrimidin-6-yl]-, O-[2-n-propylthio-4-hydroxy-pyrimidin-6-yl]-, O-[2-iso-propylthio-4-hydroxy-pyrimidin-6-yl]-, O-[2-dimethylamino-4-hydroxy-pyrimidin-6-yl]-, O-[2-diethylamino-4-hydroxy-pyrimidin-6-yl]-, O-[2-phenyl-4-hydroxy-pyrimidin-6-yl]-, O-[5-methyl-4-hydroxy-pyrimidin-6-yl]-, O-[5-chloro-4-hydroxy-pyrimidin-6- yl]-, O-[5-bromo-4-hydroxy-pyrimidin-6-yl]-, O-[2,5-dimethyl-4-hydroxy-pyrimidin-6-yl], O-[2-ethyl-5-methyl-4-hydroxy-pyrimidin-6-yl]-, O-[2-n-propyl-5-methyl-4-hydroxy-pyrimidin-6-yl]-, O-[2-iso-propyl-5-methyl-4-hydroxy-pyrimidin-6-yl]-, O-[2-n-butyl-5-methyl-4-hydroxy-pyrimidin-6-yl]-, O-[2-iso-butyl-5-methyl-4-hydroxy-pyrimidin-6-yl]-, O-[2-sec.-butyl-5-methyl-4-hydroxy-pyrimidin-6-yl]-, O-[2-tert.-butyl-5-methyl-4-hydroxy-pyrimidin-6-yl]-, O-[2-methoxy-5-methyl-4-hydroxy-pyrimidin-6-yl]-, O-[2-ethoxy-5-methyl-4-hydroxy-pyrimidin-6-yl]-, O-[2-n-propoxy-5-methyl-4-hydroxy-pyrimidin-6-yl]-, O-[2-iso-propoxy-5-methyl-4-hydroxy-pyrimidin-6-yl]-, O-[2-n-butoxy-5-methyl-4-hydroxy-pyrimidin-6-yl]-, O-[2-iso-butyl-5-methyl-4-hydroxy-pyrimidin-6-yl]-, O-[2-sec.-butoxy-5-methyl-4-hydroxy-pyrimidin-6-yl]-, O-[2-tert.-butoxy-5-methyl-4-hydroxy-pyrimidin-6-yl]-, O-[2-methylthio-5-methyl-4-hydroxy-pyrimidin-6-yl]-, O-[2-ethyl-thio-5-methyl-4-hydroxy-pyrimidin-6-yl]-, O-[2-n-propyl-thio-5-methyl-4-hydroxy-pyrimidin-6-yl]-, O-[2-iso-propylthio-5-methyl-4-hydroxy-pyrimidin-6-yl]-, O-[2-dimethylamino-5-methyl-4-hydroxy-pyrimidin-6-yl]-, O-[2-diethylamino-5-methyl-4-hydroxy-pyrimidin-6-yl]-, O-[2-phenyl-5-methyl-4-hydroxy-pyrimidin-6-yl]-, O-[2-methyl-5-chloro-4-hydroxy-pyrimidin-6-yl]-, O-[2-ethyl-5-chloro-4-hydroxy-pyrimidin-6-yl]-, O-[2-n-propyl-5-chloro-4-hydroxy-pyrimidin-6-yl]-, O-[2-iso-propyl-5-chloro-4-hydroxy-pyrimidin-6-yl]-, O-[2-n-butyl-5-chloro-4-hydroxy-pyrimidin-6-yl]-, O-[2-iso-butyl-5-chloro-4-hydroxy-pyrimidin-6-yl]-, O-[2-sec.-butyl-5-chloro-4-hydroxy-pyrimidin-6-yl]-, O-[2-tert.-butyl-5-chloro-4-hydroxy-pyrimidin-6-yl]-, O-[2-ethoxy-5-chloro-4-hydroxy-pyrimidin-6-yl]-, O-[2-methoxy-5-chloro-4-hydroxy-pyrimidin-6-yl]-, O-[2-n-propoxy-5-chloro-4-hydroxy-pyrimidin-6-yl]-, O-[2-iso-propoxy-5-chloro-4-hydroxy-pyrimidin-6-yl]-, O-[2-n-butoxy-5-chloro-4-hydroxy-pyrimidin-6-yl]-, O-[2-iso-butoxy-5-chloro-4-hydroxy-pyrimidin-6-yl]-, O-[2-sec.-butoxy-5-chloro-4-hydroxy-pyrimidin-6-yl]-, O-[2-tert.-butoxy-5-chloro-4-hydroxy-pyrimidin-6-yl]-, O-(2-methyl-thio-5-chloro-4-hydroxy-pyrimidin-6-yl]-, O-[2-ethylthio-5-chloro-4-hydroxy-pyrimidin-6-yl]-, O-[2-n-propylthio-5-chloro-4-hydroxy-pyrimidin-6-yl]-, O-[2-iso-propylthio-5-chloro-4-hydroxy-pyrimidin-6-yl]-, O-[2-dimethylamino-5-chloro-4-hydroxy-pyrimidin-6-yl]-, O-[2-diethylamino-5-chloro-4-hydroxy-pyrimidin-6-yl]-, O-[2-phenyl-5-chloro-4-hydroxy-pyrimidin-6-yl]-, O-[2-methyl-5-bromo-4-hydroxy-pyrimidin-6-yl]-, O-[2-ethyl-5-bromo-4-hydroxy-pyrimidin-6-yl]-, O-[2-n-propyl-5-bromo-4-hydroxy-pyrimidin-6-yl]-, O-[2-iso-propyl-5-bromo-4-hydroxy-pyrimidin-6-yl]-, O-[2-n-butyl-5-bromo-4-hydroxy-pyrimidin-6-yl]-, O-[2-iso-butyl-5-bromo-4-hydroxy-pyrimidin-6-yl]-, O-[2-sec.-butyl-5-bromo-4-hydroxy-pyrimidin-6-yl]-, O-[2-tert.-butyl-5-bromo-4-hydroxy-pyrimidin-6-yl]-, O-[2-methoxy-5-bromo-4-hydroxy-pyrimidin-6-yl]-, O-[2-ethoxy-5-bromo-4-hydroxy-pyrimidin-6-yl]-, O-[2-n-propoxy-5-bromo-4-hydroxy-pyrimidin-6-yl]-, O-[2-iso-propoxy-5-bromo-4-hydroxy-pyrimidin-6-yl]-, O-[2-n-butoxy-5-bromo-4-hydroxy-pyrimidin-6-yl]-, O-[2-iso-butoxy-5-bromo-4-hydroxy-pyrimidin-6-yl]-, O-[2-sec.-butoxy-5-bromo-4-hydroxy-pyrimidin-6-yl]-, O-[2-tert.-butoxy-5-bromo-4-hydroxy-pyrimidin-6-yl]-, O-[2-methylthio-5-bromo-4-hydroxy-pyrimidin-6-yl]-, O-[2-ethylthio-5-bromo-4-hydroxy-pyrimidin-6-yl]-, O-[2-n-propylthio-5-bromo-4-hydroxy-pyrimidin-6-yl]-, O-[2-iso-propylthio-5-bromo-4-hydroxy-pyrimidin-6-yl]-, O-[2-dimethylamino-5-bromo-4-hydroxy-pyrimidin-6-yl]-, O-[2-diethylamino-5-bromo-4-hydroxy-pyrimidin-6-yl]-, and O-[2-phenyl-5-bromo-4-hydroxy-pyrimidin-6-yl]-N,N-dimethyl- and -N,N-diethylcarbamic acid ester.

Both variants of the process for the preparation of the compounds according to the invention are preferably carried out in the presence of a suitable solvent or diluent. Virtually all inert organic solvents can be used for this purpose, especially aliphatic and aromatic, optionally chlorinated, hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly successful, as have aliphatic, aromatic or heterocyclic amines, for example triethylamine, trimethylamine, dimethylaniline, dimethylbenzylamine and pyridine.

The reaction temperature for both process variants can be varied within a substantial range. In general, the reaction is carried out at from 0° to 120° C., preferably at from 35° to 60° C.

In general, the reaction is allowed to take place under normal pressure.

To carry out the process variants, the starting materials are preferably employed in equimolar amounts. An excess of one or other reactant produces no significant advantages. The reactants are in general brought together in one of the above-mentioned solvents and stirred for several hours, in most cases at an elevated temperature.

An organic solvent, for example toluene, is then added to the reaction mixture and the organic phase is worked up in the usual manner by washing, drying and distilling off the solvent.

The new compounds are obtained in the form of oils which, in a number of cases, cannot be distilled without decomposition but are freed from the last volatile constituents by so-called "incipient distillation", that is to say by prolonged heating under reduced pressure to moderately elevated temperatures, and are purified in this manner. They are characterised by the refractive index.

As already mentioned, the compounds according to the present invention are distinguished by an excellent insecticidal and acaricidal activity. They are therefore active against plant pests, pests harmful to health and pests of stored products and combine a low phytotoxicity with a good action against sucking and biting insects and against mites.

For this reason, the compounds according to the invention can be employed successfully as pesticides in plant protection and in the hygiene field and the field of protection of stored products.

The compounds according to the present invention can also be used in the field of veterinary medicine since they are also active against animal parasites, in particular ectoparasites.

The active compounds are well tolerated by plants, have a favorable level of toxicity to warm-blooded animals, and can be used for combating arthropod pests, especially insects and acarids, which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera spec.;* from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blatella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The present invention also provides an arthropodicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids) which comprises applying to the arthropods, or to a habitat thereof, a compound of the present invention alone or in the form of a composition containing as active ingredient a compound of the present invention in admixture with a diluent or carrier.

The present invention further provides crops protected from damage by arthropods by being grown in areas in which immediately prior to and/or during the time of the growing a compound of the present invention was applied alone or in admixture with a diluent or carrier.

It will be seen that the usual methods of providing a harvested crop may be improved by the present invention.

The following examples illustrate preparation of the novel compounds:

EXAMPLE 1

(a) The 6-hydroxy-pyrimidinyl(thiono)(thiol)-phosphoric (phosphonic)acid esters and ester-amides (II) to be used as starting materials could be prepared, for example, as follows:

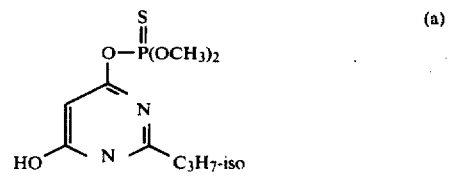

(a)

A mixture of 18.4 g (0.12 mol) of 2-isopropyl-4,6-dihydroxy-pyrimidine, 12.5 g (0.125 mol) of triethylamine and 60 ml of methylene chloride was stirred for one hour at room temperature. The reaction mixture was then cooled to about 5° C. and at this temperature 16 g (0.1 mol) of O,O-dimethyl-thionophosphoric acid diester chloride were added dropwise. The mixture was then stirred for a further 20 hours at room temperature, after which it was filtered and the filtrate was evaporated in vacuo. The residue was triturated with water and the crystalline product was filtered off. 22.7 g (82% of theory) of O,O-dimethyl-O-[2-isopropyl-6-hydroxy-pyrimidin-4-yl]-thionophosphoric acid ester were thus obtained in the form of colorless crystals of melting point 123° C.

The following intermediates of the formula

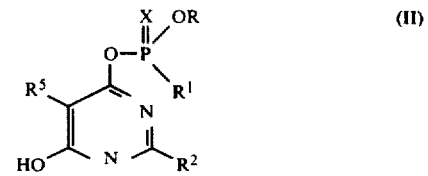

(II)

could be prepared analogously:

Table 1

| Intermediates | R | R¹ | R² | R⁵ | X | Yield (% of theory) | Physical data (refractive index: melting point, °C.) |
|---|---|---|---|---|---|---|---|
| b | $C_2H_5$ | $OC_2H_5$ | $C_3H_7$-iso | H | S | 98 | 94 |
| c | $CH_3$ | $OCH_3$ | H | H | S | 9 | 148 |
| d | $C_2H_5$ | $OC_2H_5$ | $SCH_3$ | H | S | 35 | 118 |
| e | $C_2H_5$ | $OC_2H_5$ | H | H | S | 26 | 83 |
| f | $C_3H_7$-iso | $CH_3$ | $C_3H_7$-iso | H | S | 18 | 136 |
| g | $C_2H_5$ | $C_2H_5$ | $C_3H_7$-iso | H | S | 52 | 88 |
| h | $C_2H_5$ | $OC_3H_7$-n | $C_3H_7$-iso | H | S | 60 | $n_D^{20}$:1.5168 |
| i | $C_2H_5$ | $SC_3H_7$-n | $C_3H_7$-iso | H | S | 63 | $n_D^{20}$:1.5479 |

Table 1-continued

| Intermediates | R | R¹ | R² | R⁵ | X | Yield (% of theory) | Physical data (refractive index: melting point,°C. |
|---|---|---|---|---|---|---|---|
| j | $C_2H_5$ | (phenyl) | $C_3H_7$-iso | H | S | 75 | 116 |
| k | $C_2H_5$ | $OC_2H_5$ | $OC_2H_5$ | H | S | 20 | 101 |
| l | $C_2H_5$ | $OC_2H_5$ | $C_3H_7$-iso | Br | S | 43 | 117 |
| m | $C_2H_5$ | $OC_2H_5$ | $N(CH_3)_2$ | H | S | 20 | 132 |
| n | $C_2H_5$ | $OC_2H_5$ | $CH_3$ | H | S | 7 | 79 |
| o | $C_2H_5$ | $OC_2H_5$ | (phenyl) | H | S | 12 | 118 |
| p | $C_2H_5$ | $OC_2H_5$ | $C_2H_5$ | H | S | 80 | 51 |
| q | $C_2H_5$ | $NH-C_3H_7$-iso | $C_3H_7$-iso | H | S | 52 | 101 |

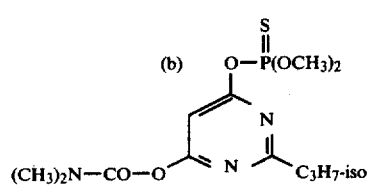

(1)

10.8 g (0.1 mol) of N,N-dimethylcarbamic acid chloride were added dropwise to a mixture of 27.8 g (0.1 mol) of O,O-dimethyl-O-[2-isopropyl-6-hydroxy-pyrimidin-4-yl]-thionophosphoric acid ester, 20.7 g (0.15 mol) of potassium carbonate and 300 ml of acetonitrile. The reaction mixture was stirred for a further 18 hours at 45°–50° C. and was then poured into 400 ml of toluene. The toluene solution was washed twice with 300 ml of water and dried over sodium sulphate, the solvent was then stripped off in vacuo and the residue was subjected to incipient distillation. 24 g (69% of theory) of O,O-dimethyl-O-[2-isopropyl-6-dimethylcarbamoyloxy-pyrimidin-4-yl]-thionophosphoric acid ester were thus obtained in the form of a yellow oil having a refractive index $n_D^{23}$ of 1.5160.

EXAMPLE 2

(a) The N,N-dialkylcarbamic acid esters (V) also to be employed as starting materials could be prepared, for example, as follows:

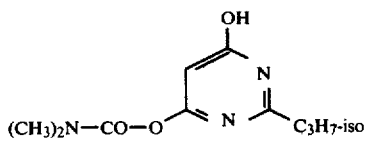

(a)

Process I 24 g (0.24 mol) of phosgene were added to a mixture of 44.8 g (0.29 mol) of 2-isopropyl-4,6-dihydroxy-pyrimidine, 30.3 g (0.3 mol) of triethylamine and 400 ml of methylene chloride at 0°–5° C. The mixture was stirred for a further hour, while cooling, and dimethylamine was then passed in at 0°–5° C. until a strongly alkaline reaction was obtained. The mixture was then stirred for 18 hours at room temperature, after which the solvent was distilled off in vacuo. The residue was triturated with water and the product which had precipitated was filtered off. 24.7 g (46% of theory) of N,N-dimethyl-O-[2-isopropyl-4-hydroxy-pyrimidin-6-yl]-carbamic acid ester were thus obtained in the form of colorless crystals of melting point 164° C.

Process II 258 g (2.4 mol) of N,N-dimethylcarbamic acid chloride were added dropwise to a boiling mixture of 308 g (2 mol) of 2-isopropyl-4,6-dihydroxyprimidine, 303 g (3 mol) of triethylamine and 1.5 liters of ethylene chloride and the reaction mixture was then boiled for a further 18 hours under reflux. Thereafter it was cooled to room temperature and the triethylammonium chloride was filtered off and rinsed with about 1 liter of ethylene chloride. The filtrate was shaken twice with 300 ml of water, the organic phase was dried over sodium sulphate and the solvent was distilled off in vacuo. 220 g (49% of theory) of N,N-dimethyl-O-[2-isopropyl-4-hydroxy-pyrimidin-6-yl]-carbamic acid ester remained.

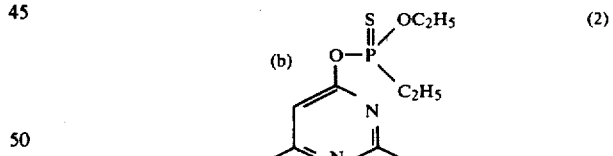

(2)

17.3 g (0.1 mol) of O-ethyl-ethanethionophosphonic acid ester chloride were added dropwise to a mixture of 22.5 g (0.1 mol) of N,N-dimethyl-O-[2-isopropyl-4-hydroxy-pyrimidin-6-yl]-carbamic acid ester, 20.7 g (0.15 mol) of potassium carbonate and 300 ml of acetonitrile and the reaction mixture was stirred for a further 4 hours at 45° C. and then poured into 400 ml of toluene. The toluene solution was washed twice with 300 ml of water and dried over sodium sulphate, the solvent was then stripped off in vacuo and the residue was subjected to incipient distillation. 20.2 g (56% of theory) of O-ethyl-O-[2-isopropyl-6-dimethylcarbamoyloxy-pyrimidin-4-yl]-thionoethanephosphonic acid ester were thus obtained in the form of a yellow oil having a refractive index $n_D^{20}$ of 1.5186.

The following compounds of the formula

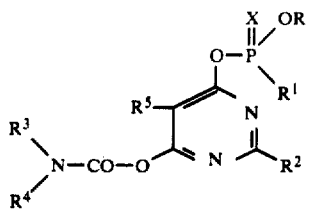
(I)

could be prepared analogously to Examples 1 and 2:

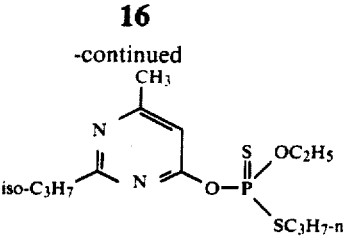

EXAMPLE 3

Table 2

| Compound | R | R$^1$ | R$^2$ | R$^3$ | R$^4$ | R$^5$ | X | Yield (% of theory) | Refractive index |
|---|---|---|---|---|---|---|---|---|---|
| 3 | C$_2$H$_5$ | OC$_2$H$_5$ | C$_3$H$_7$-iso | CH$_3$ | CH$_3$ | H | S | 86 | n$_D^{23}$:1.5370 |
| 4 | C$_3$H$_7$-iso | CH$_3$ | C$_3$H$_7$-iso | CH$_3$ | CH$_3$ | H | S | 61 | n$_D^{28}$:1.5121 |
| 5 | C$_2$H$_5$ | OC$_2$H$_5$ | CH$_3$ | CH$_3$ | CH$_3$ | H | S | 91 | n$_D^{24}$:1.5061 |
| 6 | C$_2$H$_5$ | OC$_2$H$_5$ | H | CH$_3$ | CH$_3$ | H | S | 79 | n$_D^{23}$:1.5115 |
| 7 | C$_2$H$_5$ | OC$_2$H$_5$ | (phenyl) | CH$_3$ | CH$_3$ | H | S | 75 | n$_D^{22}$:1.5611 |
| 8 | C$_2$H$_5$ | OC$_2$H$_5$ | C$_2$H$_5$ | CH$_3$ | CH$_3$ | H | S | 72 | n$_D^{22}$:1.5089 |
| 9 | C$_2$H$_5$ | OC$_2$H$_5$ | SCH$_3$ | CH$_3$ | CH$_3$ | H | S | 75 | n$_D^{22}$:1.5465 |
| 10 | C$_2$H$_5$ | OC$_2$H$_5$ | OC$_2$H$_5$ | CH$_3$ | CH$_3$ | H | S | 78 | n$_D^{22}$:1.5121 |
| 11 | C$_2$H$_5$ | OC$_2$H$_5$ | C$_3$H$_7$-iso | CH$_3$ | CH$_3$ | H | O | 35 | n$_D^{26}$:1.4670 |
| 12 | C$_2$H$_5$ | NH—C$_3$H$_7$-iso | C$_3$H$_7$-iso | CH$_3$ | CH$_3$ | H | S | 87 | n$_D^{24}$:1.5134 |
| 13 | C$_2$H$_5$ | SC$_3$H$_7$-n | C$_3$H$_7$-iso | CH$_3$ | CH$_3$ | H | S | 84 | n$_D^{23}$:1.5298 |
| 14 | C$_2$H$_5$ | (phenyl) | C$_3$H$_7$-iso | CH$_3$ | CH$_3$ | H | S | 54 | n$_D^{21}$:1.5462 |
| 15 | C$_2$H$_5$ | OC$_2$H$_5$ | N(CH$_3$)$_2$ | CH$_3$ | CH$_3$ | H | S | 56 | n$_D^{21}$:1.5235 |
| 16 | C$_2$H$_5$ | OC$_2$H$_5$ | C$_3$H$_7$-iso | C$_2$H$_5$ | C$_2$H$_5$ | H | S | 89 | n$_D^{19}$:1.5012 |
| 17 | CH$_3$ | OCH$_3$ | C$_3$H$_7$-iso | C$_2$H$_5$ | C$_2$H$_5$ | H | S | 74 | n$_D^{19}$:1.5213 |
| 18 | CH$_3$ | CH$_3$ | C$_3$H$_7$-iso | CH$_3$ | CH$_3$ | H | S | 85 | n$_D^{21}$:1.5238 |
| 19 | C$_2$H$_5$ | CH$_3$ | C$_3$H$_7$-iso | CH$_3$ | CH$_3$ | H | S | 86 | n$_D^{21}$:1.5189 |
| 20 | CH$_3$ | C$_2$H$_5$ | C$_3$H$_7$-iso | CH$_3$ | CH$_3$ | H | S | 82 | n$_D^{21}$:1.5209 |
| 21 | C$_2$H$_5$ | OC$_2$H$_5$ | N(CH$_3$)$_2$ | CH$_3$ | CH$_3$ | CH$_3$ | S | | |
| 22 | C$_2$H$_5$ | OC$_2$H$_5$ | C$_3$H$_7$-iso | CH$_3$ | CH$_3$ | Cl | S | | |
| 23 | C$_2$H$_5$ | OC$_2$H$_5$ | C$_3$H$_7$-iso | CH$_3$ | CH$_3$ | Br | S | | |

The insecticidal and acaricidal activity of the compounds of this invention is illustrated by the following examples wherein the compounds according to the present invention are each identified by the number (given in brackets) from the preparative examples hereinabove.

The known comparison compounds are identified as follows:

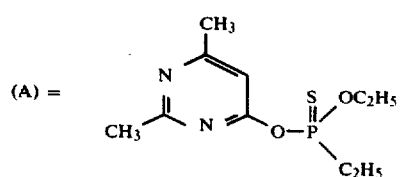

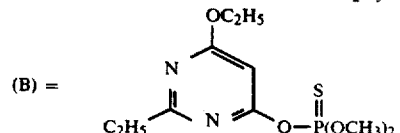

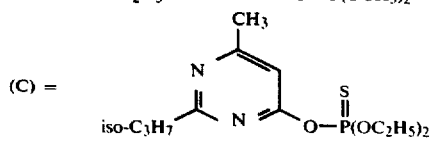

Plutella test
Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamondback moth (*Plutella maculipennis*).

After the specified periods of time, the degree of destruction was determined as a percentage: 100% meant that all of the caterpillars were killed whereas 0% meant that none of the caterpillars were killed.

The active compounds, the concentrations of the active compounds, the evaluation times and the results can be seen from the following table:

Table 3

| | (Insects which damage plants) Plutella test | |
|---|---|---|
| Active compounds | Active compound concentration in % | Destruction in % after 3 days |
| (A) | 0.1 | 100 |

Table 3-continued

| Active compounds | (Insects which damage plants) Plutella test | |
|---|---|---|
| | Active compound concentration in % | Destruction in % after 3 days |
| | 0.01 | 0 |
| (6) | 0.1 | 100 |
| | 0.01 | 100 |
| (5) | 0.1 | 100 |
| | 0.01 | 100 |
| (10) | 0.1 | 100 |
| | 0.01 | 100 |
| (8) | 0.1 | 100 |
| | 0.01 | 100 |
| (15) | 0.1 | 100 |
| | 0.01 | 100 |
| (3) | 0.1 | 100 |
| | 0.01 | 100 |
| (1) | 0.1 | 100 |
| | 0.01 | 100 |
| (2) | 0.1 | 100 |
| | 0.01 | 100 |
| (13) | 0.1 | 100 |
| | 0.01 | 100 |
| (4) | 0.1 | 100 |
| | 0.01 | 100 |

EXAMPLE 4

Tetranychus test (resistant)

Solvent: 3 parts by weight of acetone

Emulsifier: 1 part by weight of alkylaryl polyglycol ether

To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all of the spider mites were killed whereas 0% meant that none of the spider mites were killed.

The active compounds, the concentrations of the active compounds, the evaluation times and the results can be seen from the following table:

Table 4

| Active compounds | (Mites which damage plants) Tetranychus test | |
|---|---|---|
| | Active compound concentration in % | Destruction in % after 2 days |
| (B) | 0.1 | 98 |
| | 0.01 | 0 |
| (C) | 0.1 | 95 |
| | 0.01 | 0 |
| (D) | 0.1 | 98 |
| | 0.01 | 0 |
| (6) | 0.1 | 100 |
| | 0.01 | 60 |
| (1) | 0.1 | 100 |
| | 0.01 | 80 |
| (4) | 0.1 | 100 |
| | 0.01 | 100 |

It will be appreciated that the instant specification and examples are set forth by way of illustration and not limitation, and that various modifications and changes may be made without departing from the spirit and scope of the present invention.

What we claim is:

1. An O-alkyl-O-(6-dialkylcarbamoyloxy-pyrimidin-4-yl)-(thiono)(thiol)-phosphoric(phosphonic) acid ester or ester-amide of the formula

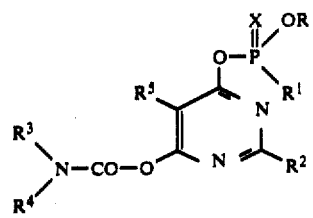

in which
R is alkyl with 1 to 6 carbon atoms,
$R^1$ is alkyl or alkoxy with 1 to 5 carbon atoms, alkylthio or alkylamino with 1 to 6 carbon atoms, or phenyl,
$R^2$ is hydrogen, alkyl or alkoxy with 1 to 6 carbon atoms, alkylthio or alkylamino with 1 to 5 carbon atoms, or phenyl,
$R^3$ and $R^4$ each independently is alkyl with 1 to 4 carbon atoms,
$R^5$ is hydrogen, methyl or halogen, and
X is oxygen or sulphur.

2. A compound according to claim 1, in which
R is alkyl with 1 to 6 carbon atoms,
$R^1$ is alkyl or alkoxy each with 1 to 5 carbon atoms, alkylthio or monoalkylamino each with 1 to 6 carbon atoms, or phenyl,
$R^2$ is hydrogen, phenyl, alkyl or alkoxy each with 1 to 6 carbon atoms, or atoms per alkyl moiety.
$R^3$ and $R^4$ each is alkyl with 1 to 4 carbon atoms,
$R^5$ is hydrogen, methyl, chlorine or bromine, and
X is sulphur.

3. A compound according to claim 1, wherein such compound is O,O-dimethyl-O-[2-isopropyl-6-dimethylcarbamoyloxypyrimidin-4-yl]-thionophosphoric acid ester of the formula

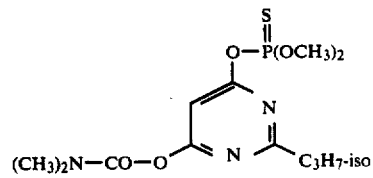

4. A compound according to claim 1, wherein such compound is O-ethyl-O-[2-isopropyl-6-dimethylcarbamoyloxypyrimidin-4-yl]-thionoethanephosphonic acid ester of the formula

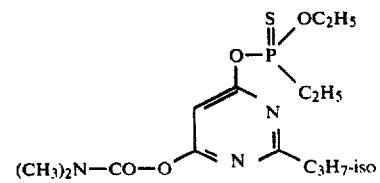

5. A compound according to claim 1, wherein such compound is O,O-diethyl-O-[2-isopropyl-6-dimethylcarbamoyloxypyrimidin-4-yl]-thionophosphoric acid ester of the formula

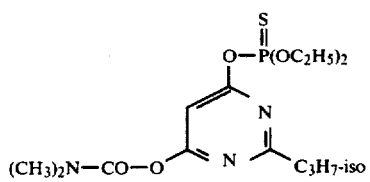

6. A compound according to claim 1, wherein such compound is O-isopropyl-O-[2-isopropyl-6-dimethyl-carbamoyloxypyrimidin-4-yl]-thionomethanephosphonic acid ester of the formula

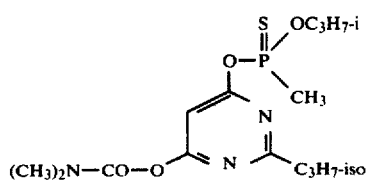

7. A compound according to claim 1, wherein such compound is O,O-diethyl-O-[2-ethoxy-6-dimethyl-carbamoyloxypyrimidin-4-yl]-thionophosphoric acid ester of the formula

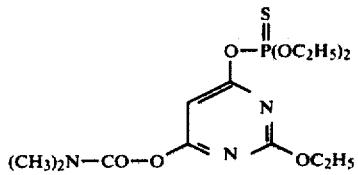

8. An arthropodicidal composition containing as active ingredient an arthropodicidally effective amount of a compound according to claim 1 in admixture with a diluent.

9. A method of combating arthropods, which comprises applying to the arthropods or to a habitat thereof, an arthropodically effective amount of a compound according to claim 1.

10. The method according to claim 9, in which said compound is

O,O-dimethyl-O-[2-isopropyl-6-dimethylcarbamoyloxy-pyrimidin-4-yl]-thionophosphoric acid ester, O-ethyl-O-[2-isopropyl-6-dimethylcarbamoyloxypyrimidin-4-yl]-thionoethanephosphonic acid ester, O,O-diethyl-O-[2-isopropyl-6-dimethyl-carbamoyloxypyrimidin-4-yl]-thionophosphoric acid ester, O-isopropyl-O-[2-isopropyl-6-dimethylcarbamoyloxypyrimidin-4-yl]-thionomethanephosphonic acid ester or O,O-diethyl-O-[2-ethoxy-6-dimethyl-carbamoyloxypyrimidin-4-yl]-thionophosphonic acid ester.

* * * * *